United States Patent [19]

Leifeld

[11] Patent Number: 5,018,246

[45] Date of Patent: May 28, 1991

[54] PASSAGE WIDTH ADJUSTING DEVICE FOR A SLIVER TRUMPET

[75] Inventor: Ferdinand Leifeld, Kempen, Fed. Rep. of Germany

[73] Assignee: Trützschler GmbH & Co. KG, Monchen-Gladbach, Fed. Rep. of Germany

[21] Appl. No.: 513,671

[22] Filed: Apr. 24, 1990

[30] Foreign Application Priority Data

Apr. 25, 1989 [DE] Fed. Rep. of Germany ....... 3913548

[51] Int. Cl.$^5$ .............................................. D01G 15/46
[52] U.S. Cl. .................................................. 19/150
[58] Field of Search ........................................ 19/150

[56] References Cited

U.S. PATENT DOCUMENTS

| 143,508 | 10/1873 | Good | 19/150 |
|---|---|---|---|
| 146,816 | 1/1874 | Frye | 19/150 |
| 190,422 | 5/1877 | Dawson | 19/150 |
| 614,819 | 11/1898 | Albasini | 19/150 |
| 830,290 | 9/1906 | Berger | 19/150 |
| 3,925,850 | 12/1975 | Lytton | 19/150 X |
| 4,864,853 | 9/1989 | Grunder et al. | |

FOREIGN PATENT DOCUMENTS

| 1510487 | 3/1971 | Fed. Rep. of Germany . | |
|---|---|---|---|
| 2358941 | 6/1975 | Fed. Rep. of Germany . | |
| 1949930 | 8/1977 | Fed. Rep. of Germany . | |
| 8704472 | 7/1987 | PCT Int'l Appl. . | |
| 531578 | 1/1973 | Switzerland | 19/150 |
| 524887 | 8/1940 | United Kingdom | 19/150 |
| 729210 | 5/1955 | United Kingdom . | |
| 1029872 | 5/1966 | United Kingdom . | |
| 1372513 | 10/1974 | United Kingdom . | |

*Primary Examiner*—W. C. Reynolds
*Assistant Examiner*—John J. Calvert
*Attorney, Agent, or Firm*—Spencer & Frank

[57] ABSTRACT

A sliver producing textile machine includes a sliver trumpet having a wall defining a constriction through which the sliver passes. A sensor is arranged at the constriction for determining the thickness and irregularities in the sliver passing through the constriction. The wall includes a stationary wall portion and a movable wall portion which is displaceable relative to the stationary wall portion for varying the size of the cross-sectional area of the constriction.

10 Claims, 5 Drawing Sheets

PASSAGE WIDTH ADJUSTING DEVICE FOR A SLIVER TRUMPET

CROSS REFERENCE TO RELATED APPLICATION

This application claims the priority of Federal Republic of Germany application No. P 39 13 548.9 filed Apr. 25, 1989, which is incorporated herein by reference.

BACKGROUND OF THE INVENTION

This invention relates to a passage width adjustment of a sliver trumpet which is associated with a measuring device for determining the thickness and irregularities of a running fiber sliver, particularly in spinning preparation machines such as carding machines. The measuring member is installed in the sliver trumpet which, in turn, serves for compressing (densifying) the through-going sliver.

For different sliver numbers the sliver trumpet must have different constrictions (outlet openings) in the zone of the sliver sensor. In a device disclosed in published European application 252,952, at the sliver trumpet a measuring member is arranged which senses the thickness and irregularities of the sliver in a measuring channel. For making adjustments for different sliver numbers, the measuring channel is provided in a replaceable measuring component mounted in the sliver trumpet. Thus, in this arrangement, the measuring component is replaced ever time the sliver number is changed. Such a replacement of the sensor location proper is circumstantial, expensive and repeatedly requires compensation measures.

SUMMARY OF THE INVENTION

It is an object of the invention to provide an improved trumpet passage adjusting arrangement from which the discussed disadvantages are eliminated and which, in particular, makes possible in a simple manner the adaption of the constriction of the trumpet to varying sliver numbers and further allows an extension of the measuring range of the measuring organ.

This object and others to become apparent as the specification progresses, are accomplished by the invention, according to which, briefly stated, in the zone of its constriction the sliver trumpet has a movably supported wall element or wall portion with which the inner width (that is, the cross-sectional area) of the constriction may be adjusted.

By virtue of the projection of the movable wall element into the constriction of the sliver trumpet there is achieved an adaption of the constriction to different sliver numbers in a structurally and operationally simple manner. It is particularly of advantage that the wall element, such as a slide member, changes the measuring force. The movable wall element cooperates with the measuring organ, for example, a sensor tongue and in this manner enlarges the measuring range of the measuring organ in a multiple manner. By virtue of the invention, a replacement of the entire measuring components in case of different sliver numbers is no longer necessary and at the same time, a significant enlargement of the measuring range is possible in an advantageous manner. Also, the conversion period upon change of sliver numbers is significantly reduced and maintenance work is simplified.

BRIEF DESCRIPTION OF THE DRAWING

FIG. 9b is a perspective view of the construction shown in FIG. 9a.

DESCRIPTION OF THE PREFERRED EMBODIMENTS

Figure 1:
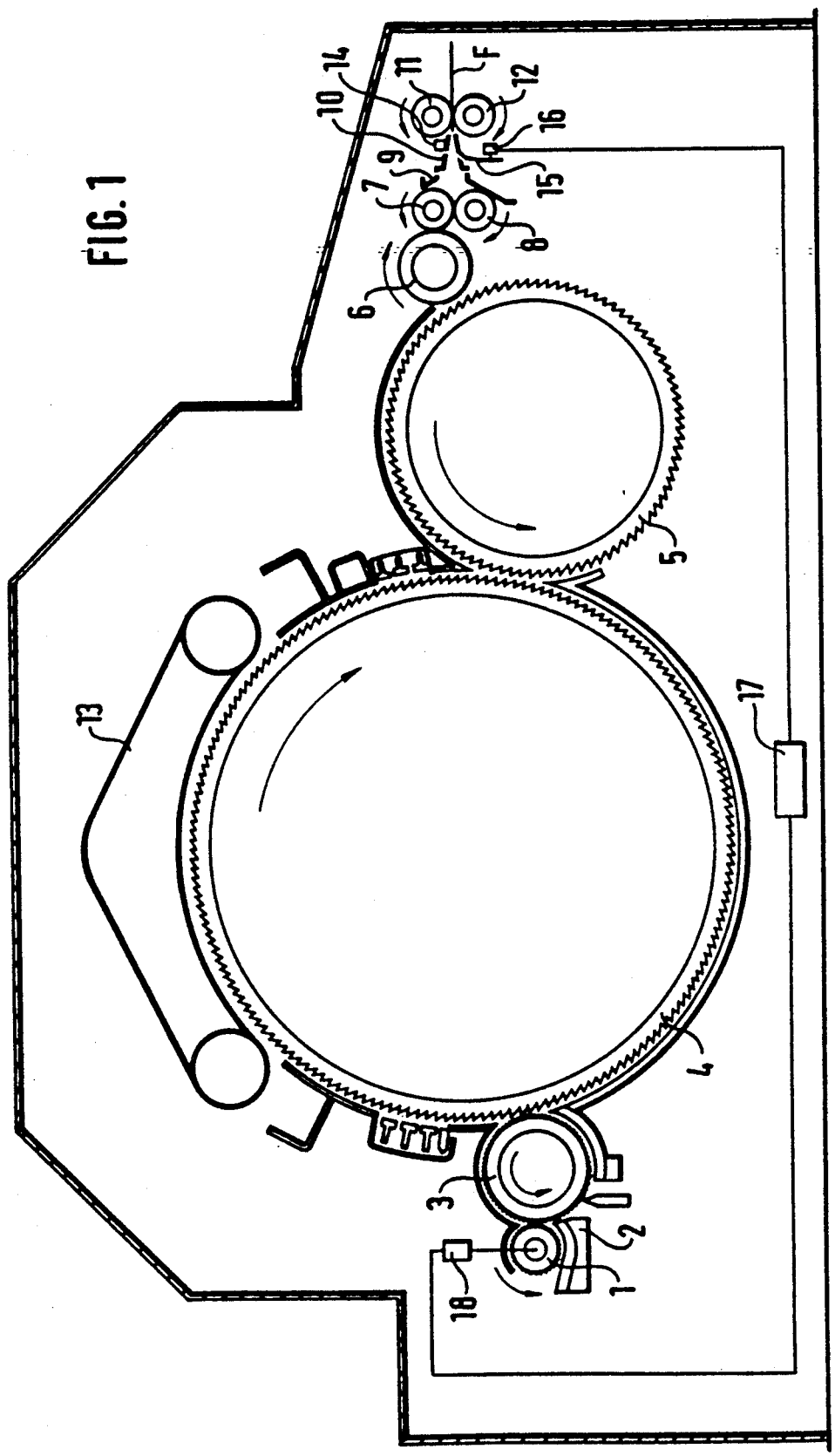
FIG. 1 is a schematic side elevational view of a carding machine incorporating a preferred embodiment of the invention.

Turning to FIG. 1, there is illustrated therein a known carding machine which may be an EXACTA-CARD DK 740 Model manufactured by Trützschler GmbH & Co. KG, Mönchengladbach, Federal Republic of Germany. The carding machine has a feed roller 1, a feed table 2, a licker-in 3, a main carding cylinder 4, a doffer 5, a stripping roller 6, crushing rollers 7 and 8, a web guide element 9, a sliver trumpet 10, calender rollers 11 and 12 as well as travelling flats 13. The sliver trumpet 10 includes a movable wall element 14 to be described below in more detail, and a sensor tongue 15 coupled with an inductive proximity initiator 16 which applies signals to a regulator 17. The latter, in turn, controls a drive motor 18 of the feed roller 1.

Figure 2:
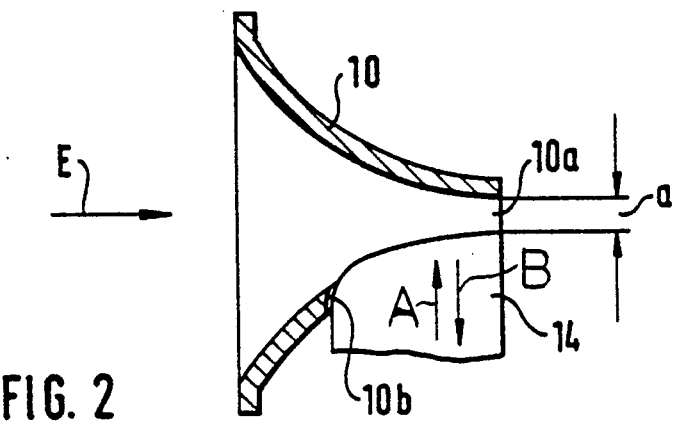
FIG. 2 is a schematic sectional side elevational view of the embodiment shown in FIG. 1 showing more details.

Turning to FIG. 2, in the preferred embodiment of the invention illustrated therein the wall of the sliver trumpet 10 has, in the zone of the constriction 10a (trumpet outlet), an opening 10b through which projects the wall element 14 which completely fills the aperture 10b and thus constitutes that wall portion of the trumpet 10 which has been removed to provide the opening 10b. The inner width a (or, stated differently, the cross-sectional area) of the constriction 10a is variable by virtue of the adjustability of the movable wall element 14 in the direction of arrows A or B. The direction of sliver run through the trumpet 10 is indicated by the arrow E.

Figure 3:
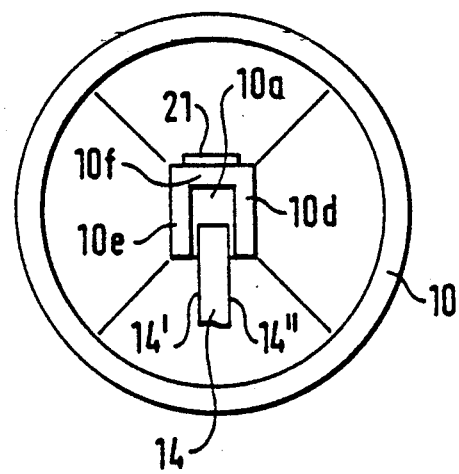
FIG. 3 is a front elevational view of the preferred embodiment as seen in the direction of the arrow E of FIG. 2.

Turning to FIG. 3, it is seen that in the zone of the constriction 10a the sliver trumpet 10 has fixed walls 10d, 10e, 10f forming together a generally U-shaped, angular configuration. The movable wall element 14 closes the opening of the "U", whereby the constriction 10a has a closed, rectangular shape. The wall element 14 has two parallel side faces 14' and 14''. At the outer face of the fixed wall 10f there is arranged a measuring element, constituted by an expansion measuring strip (strain gauge) 21 which responds to thickness variations of the running sliver (not shown) passing through the constriction 10a and which is coupled to a transducer (also not shown). In the alternative, the measuring element may be a conventional force measuring box which responds to stresses in the trumpet wall, derived from friction forces upon the passage of the sliver through the constriction 10a.

Figure 4:
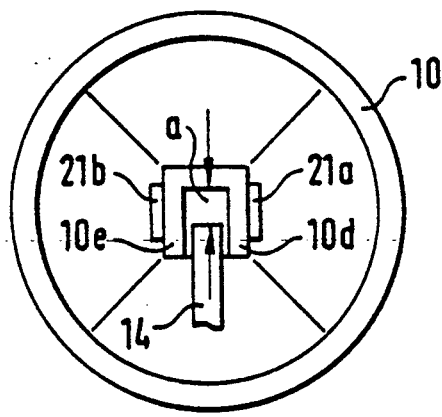
FIG. 4 is a front elevational view of another preferred embodiment of the invention.

The embodiment illustrated in FIG. 4 is similar to that shown in FIG. 3 except that two expansion measuring strips 21a and 21b are provided on respective opposite faces of fixed walls 10d and 10e.

Figure 5:
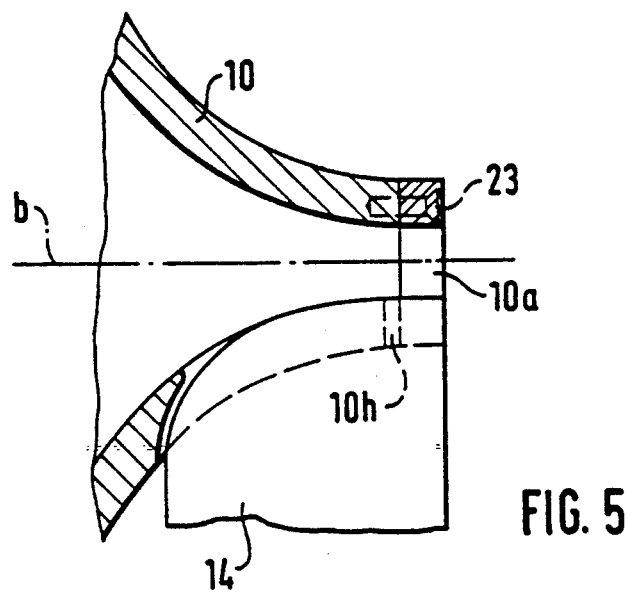
FIGS. 5-8 are sectional side elevational views of four further preferred embodiments of the invention.

Turning now to the embodiment illustrated in FIG. 5, at the outlet of the sliver trumpet 10, in the zone of its constriction 10a, a throughgoing slit 10h is provided in the trumpet wall, perpendicularly to the trumpet axis b. The arrangement according to FIGS. 3 or 4 is secured by a screw 23 to the outlet end of the sliver trumpet 10. In this manner, the fixed walls 10e and 10d are exposed to external air and may be displaced in accordance with the irregularities of the sliver.

Figure 6:
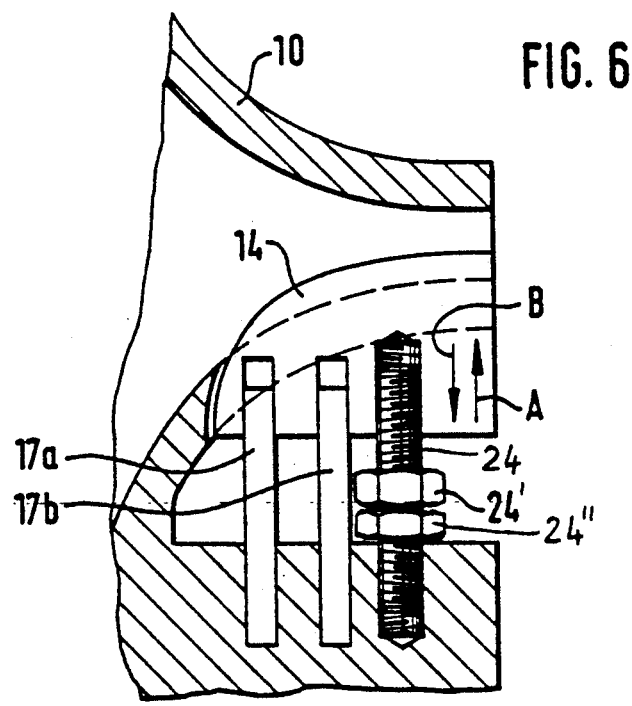

Turning to the embodiment shown in FIG. 6, the movable wall element 14 is adjustable and indicated by the arrows A and B and may be immobilized in a predetermined position to define a desired opening width of the sliver trumpet 10. In this manner, an adaption to various sliver numbers is achieved. The movable wall element 14 is supported in guides 17a, 17b. There is further provided a dual (oppositely threaded) setscrew 24 and a nut 24' affixed thereto with which a shift of the wall element 14 may be effected. Tightening the counternut 24" immobilizes the screw 24 and thus fixes the set position of the wall element 14.

Figure 7:
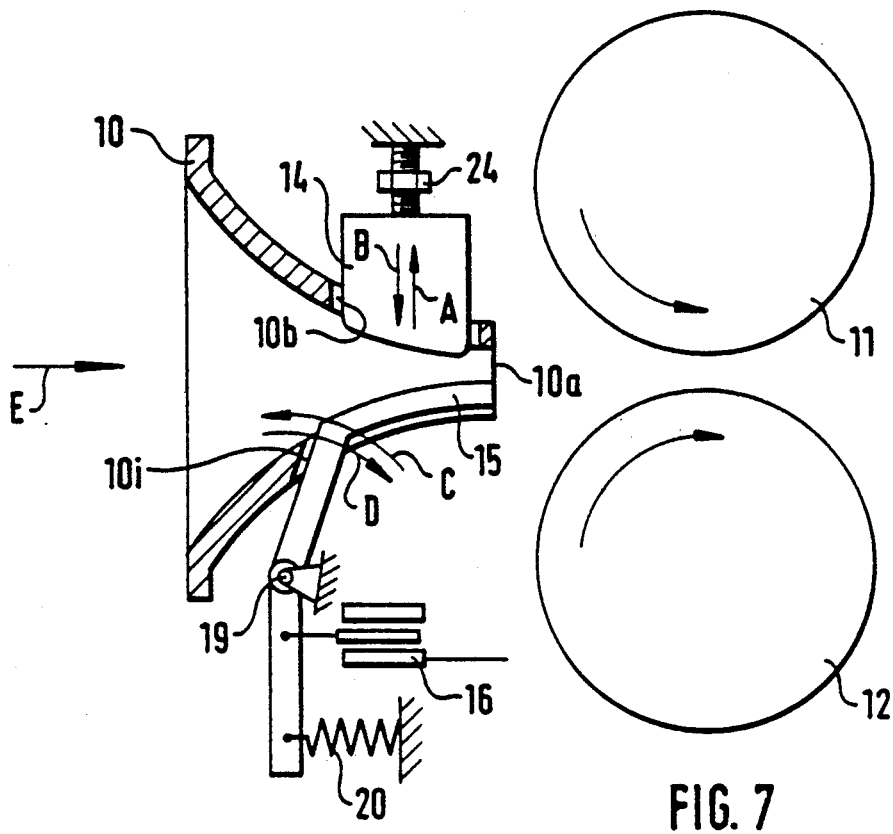

Turning to FIG. 7, there is illustrated therein a sliver trumpet 10 in which the movable wall element 14 projects through the wall opening 10b and is displaceable by a setscrew 24 in directions indicated by arrows A, B. Through a further opening 10i provided in the wall of the sliver trumpet 10 there projects, in a known manner, a sensor tongue 15 which is supported in a pivot bearing 19 for swinging motions indicated by arrows C and D. The sensor tongue 15 is biased by a spring 20 and is connected with an inductive proximity initiator 16 which converts thickness fluctuations of the sliver into electric signals. By shifting the movable wall element 14, the inner width or inner cross-sectional area of the constriction 10a is changed whereby a greater measuring sensitivity is achieved because the compressing pressure of the sliver is changed. The resolution of the measurement is improved and thus the measuring range is increased.

Figure 8:
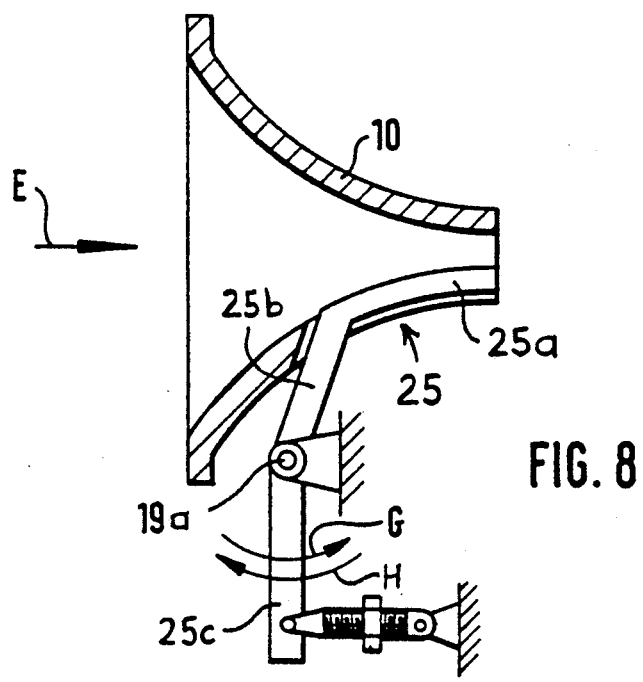

Turning to FIG. 8, there is shown a trumpet constriction adjusting element 25, which has a wall portion 25a, continuing in an arm 25b, which, in turn, continues in an arm 25c. In the junction of arms 25b and 25c the adjusting element 25 is pivotally held by a bearing 19a. The adjusting element 25 is thus pivotal in the direction of arrows G and H. The arm 25c is connected with a setscrew to adjust the angular position of the adjusting element 25.

Figure 9A:
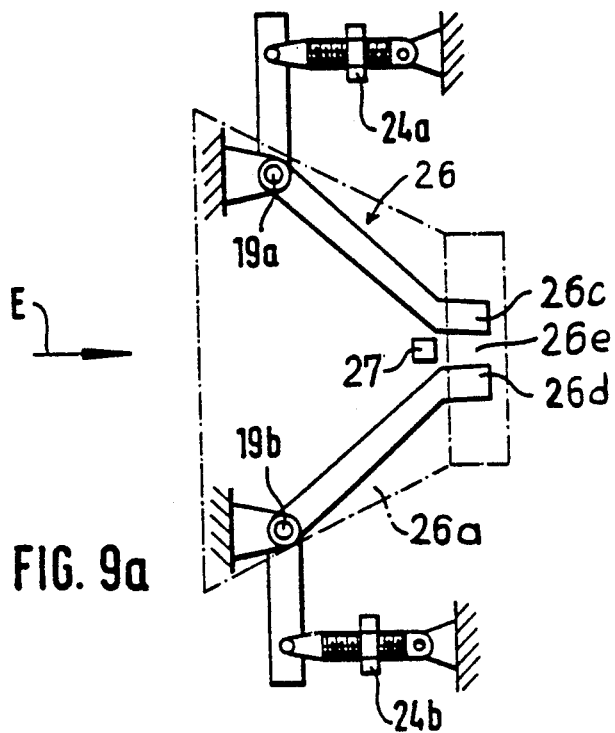
FIG. 9a is a schematic top plan view of still a further embodiment of the invention.
Figure 9B:
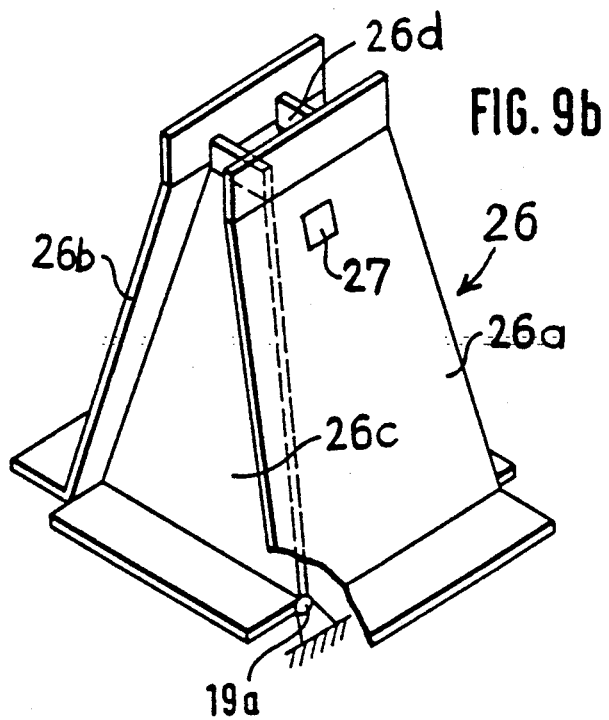

Turning now to the embodiment illustrated in FIGS. 9a and 9b, the sliver trumpet generally designated at 26 is, when viewed in cross section, of rectangular configuration. The sliver trumpet 26 has two opposite fixed planar walls 26a and 26b and two opposite movable walls 26c and 26d. the two opposite movable walls are adjustable by respective setscrews 24a and 24b for widening or narrowing the trumpet constriction 26e where a sensor 27 is arranged (in the alternative, the sensor may be a sensor tongue 15 as shown in FIG. 7). In the trumpet constriction 26e the plane of the movable wall portions 26c and 26d is generally perpendicular to the measuring plane in which the sensor operates.

It will be understood that the above description of the present invention is susceptible to various modifications, changes and adaptions, and the same are intended to be comprehended within the meaning and range of equivalents of the appended claims.

What is claimed is:

1. In a sliver producing textile machine including a sliver trumpet having wall means defining a constriction through which the sliver passes; said constriction having a cross-sectional area; and a sensor arranged at said constriction for determining the thickness and irregularities in the sliver passing through said constriction; the improvement wherein said wall means includes a stationary wall portion and a movable wall portion displaceable relative to the stationary wall portion for varying the size of said cross-sectional area; the improvement further comprising support means for linearly movably supporting said movable wall portion in a direction perpendicular to a direction of travel of the sliver.

2. A sliver producing textile machine as defined in claim 1, wherein said stationary wall portion has an aperture; said movable wall portion being disposed in said aperture.

3. A sliver producing textile machine as defined in claim 1, further comprising immobilizing means for fixing said movable wall portion in an adjusted position.

4. A sliver producing textile machine as defined in claim 1, wherein said stationary wall portion is generally U-shaped in cross section.

5. A sliver producing textile machine as defined in claim 4, wherein said cross-sectional area is shaped as a rectangle; said stationary wall portion defining three sides of the rectangle and said movable wall portion defining one side of the rectangle.

6. A sliver producing textile machine as defined in claim 1, wherein said movable wall portion has two opposite, parallel side faces.

7. A sliver producing textile machine as defined in claim 1, further comprising adjusting means for varying the position of said movable wall portion.

8. A sliver producing textile machine as defined in claim 7, wherein said adjusting means comprises a setscrew connected to said movable wall portion.

9. A sliver producing textile machine as defined in claim 1, wherein said sensor is situated externally of said trumpet at said stationary wall portion.

10. A sliver producing textile machine as defined in claim 1, wherein said sensor comprises a strain gauge attached to said wall means.

* * * * *